(12) United States Patent
Wright

(10) Patent No.: US 6,807,966 B2
(45) Date of Patent: Oct. 26, 2004

(54) OXYGEN DELIVERY SYSTEM AND METHOD OF USING SAME

(75) Inventor: Clifford A. Wright, San Diego, CA (US)

(73) Assignee: Medical Device Group, Inc.

( * ) Notice: Subject to any disclaimer, the term of this patent is extended or adjusted under 35 U.S.C. 154(b) by 29 days.

(21) Appl. No.: 10/224,849

(22) Filed: Aug. 21, 2002

(65) Prior Publication Data

US 2004/0035430 A1 Feb. 26, 2004

(51) Int. Cl.$^7$ ............................................. A61M 15/08
(52) U.S. Cl. ............................ 128/207.18; 128/200.26
(58) Field of Search .................... 128/207.18, DIG. 26, 128/207.17, 200.26, 207.14, 206.11, 204.11, 203.22; 604/174, 177

(56) References Cited

U.S. PATENT DOCUMENTS

| | | | |
|---|---|---|---|
| 2,168,705 A | | 8/1939 | Francisco et al. |
| 2,502,734 A | | 4/1950 | Lyons |
| 2,763,263 A | | 9/1956 | Ellman |
| 2,868,199 A | | 1/1959 | Hudson |
| 3,802,431 A | | 4/1974 | Farr |
| 4,106,505 A | | 8/1978 | Salter et al. |
| 4,156,426 A | | 5/1979 | Gold |
| 4,406,283 A | | 9/1983 | Bir |
| 4,422,456 A | | 12/1983 | Tiep |
| 4,465,067 A | * | 8/1984 | Koch et al. ............ 128/207.18 |
| 4,559,941 A | * | 12/1985 | Timmons et al. ...... 128/207.18 |
| 4,699,139 A | * | 10/1987 | Marshall et al. ....... 128/207.18 |
| 4,739,757 A | | 4/1988 | Edwards |
| 4,753,233 A | | 6/1988 | Grimes |
| 4,808,160 A | | 2/1989 | Timmons et al. |
| 4,836,200 A | | 6/1989 | Clark |
| 4,878,491 A | * | 11/1989 | McGilvray, III ....... 128/201.11 |
| 5,025,805 A | * | 6/1991 | Nutter ................... 128/207.18 |
| 5,117,818 A | * | 6/1992 | Palfy ..................... 128/204.11 |
| 5,185,005 A | * | 2/1993 | Ballantyne ................. 604/174 |
| 5,193,534 A | * | 3/1993 | Peppler ................. 128/207.18 |
| 5,271,391 A | | 12/1993 | Graves |
| 5,400,776 A | * | 3/1995 | Bartholomew ......... 128/200.24 |
| 5,438,979 A | | 8/1995 | Johnson, Jr. et al. |
| 5,636,630 A | | 6/1997 | Miller et al. |
| 5,682,881 A | | 11/1997 | Winthrop et al. |
| 6,298,850 B1 | | 10/2001 | Argraves |
| 6,328,038 B1 | | 12/2001 | Kessler et al. |
| 6,505,624 B1 | * | 1/2003 | Campbell, Sr. ........ 128/207.18 |
| 6,561,193 B1 | * | 5/2003 | Noble ................... 128/207.18 |

* cited by examiner

Primary Examiner—Henry Bennett
Assistant Examiner—Mital Patel

(57) ABSTRACT

A fluid delivery system includes a nasal delivery tube and an ear hook support tube that facilitates the delivery of fluids to the lungs of a user. The ear hook support tube is plugged at its distal end with an elongated flexible ear hook that is adapted to be hooked over one ear of the user. A slider support tube having an ear hook slider mounted thereon is coupled in an airtight manner to an opposite end of the nasal support tube and is adapted to be coupled to a supply of fluid, such as a supply of air. Another ear hook is mounted to the ear hook slider and is adapted to be hooked over the other ear of the user.

10 Claims, 4 Drawing Sheets

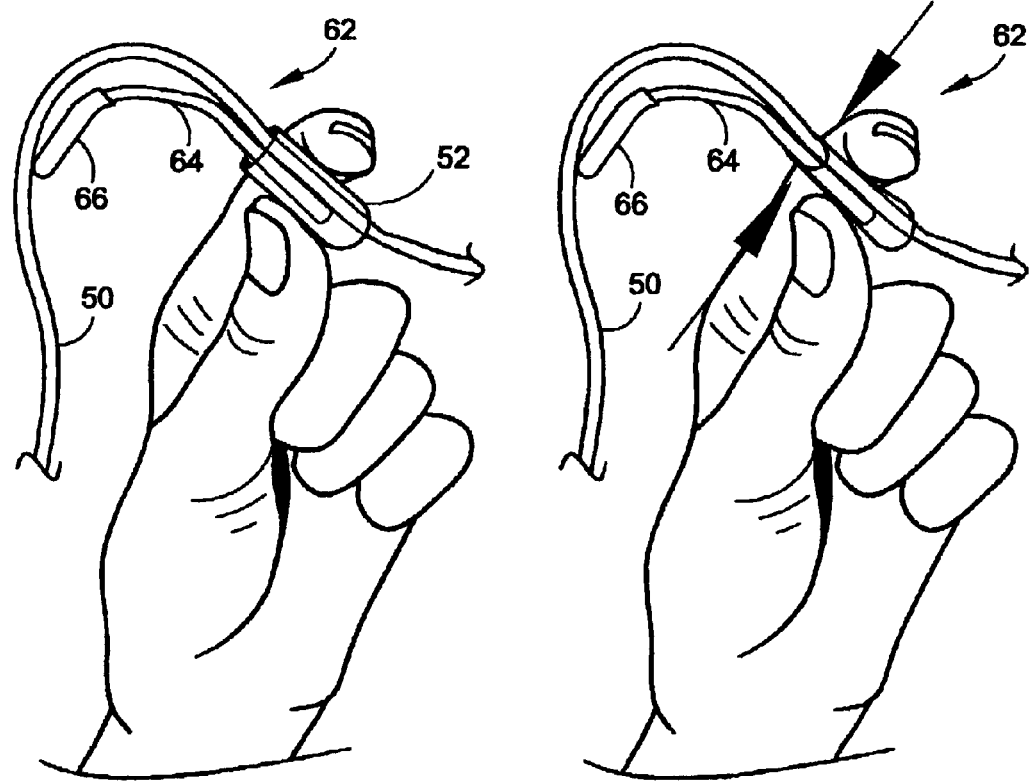
FIG. 5
FIG. 6
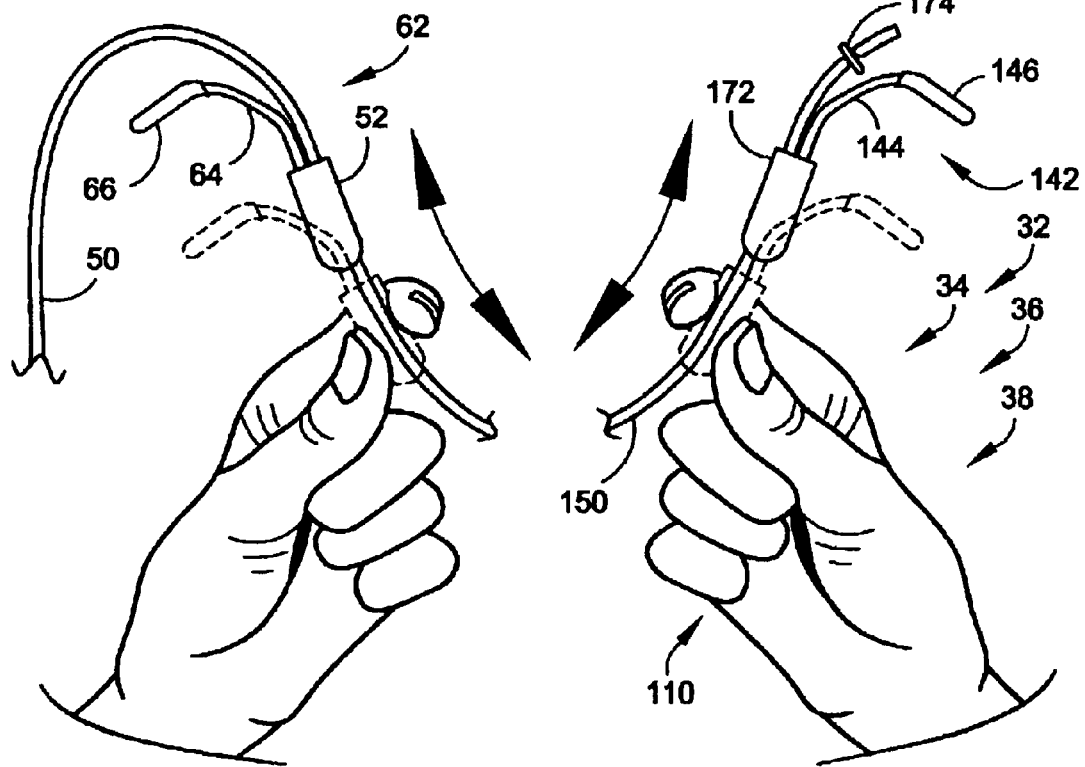
FIG. 7
FIG. 8

OXYGEN DELIVERY SYSTEM AND METHOD OF USING SAME

FIELD OF THE INVENTION

This invention relates in general to oxygen delivery systems, and more particularly to an oxygen delivery system that includes a nasal cannula having an ear hook slider and ear hooks for securing the nasal cannula at a desired position on a user.

BACKGROUND

Oxygen delivery systems that include nasal cannulas are well known in the art. Examples of such prior art systems include U.S. Pat. Nos. 6,328,038 B1; 6,298,850; 5,682,881; 5,636,630; 5,438,979; 5,271,391; 5,117,818; 5,025,805; 4,836,200; 4,808,160; 4,753,233; 4,739,757; 4,699,139; 4,422,456; 4,406,283; 4,156,426; 4,106,505; 3,802,431; 2,868,199; 2,763,263: and 2,168,705.

While nasal cannulas are a convenient method of supplying a patient with oxygen enriched gases, it would be highly desirable to have a new and improved oxygen delivery system that includes a nasal cannula that is easily adjusted for the comfort of the patient and that is not prone to falling off the face of the patient.

SUMMARY OF THE INVENTION

An oxygen-delivery system includes a nasal cannula having a pair of nasal prongs that may be sized in length for insertion into the nasal cavities of a user. The nasal cannula is plugged at its distal end with an elongated flexible ear hook that is adapted to be hooked over one ear of the user. A slider having another ear hook mounted thereto is mounted at about the proximate end of the nasal cannula that is adapted to be coupled to a low-pressure oxygen outlet. The other ear hook is adapted to be hooked over the other ear of the user in order to support the pair of nasal prongs in the nasal cavities of the user. According to the method of using the oxygen delivery system a user hooks the distal end ear hook over one ear, inserts the nasal prongs into his or her nasal cavities, and moves the ear hook slider to an adjusted position that allows the other ear hook to be securely hooked over the other ear of the user with the nasal prongs comfortably inserted into the nasal cavities of the user.

BRIEF DESCRIPTION OF THE DRAWINGS

FIGS. 5–7 depict various steps in the novel method of using the oxygen delivery system of the present invention;

FIG. 8 depicts another oxygen delivery system, which is constructed in accordance with the present invention;

DETAILED DESCRIPTION

Figure 1:
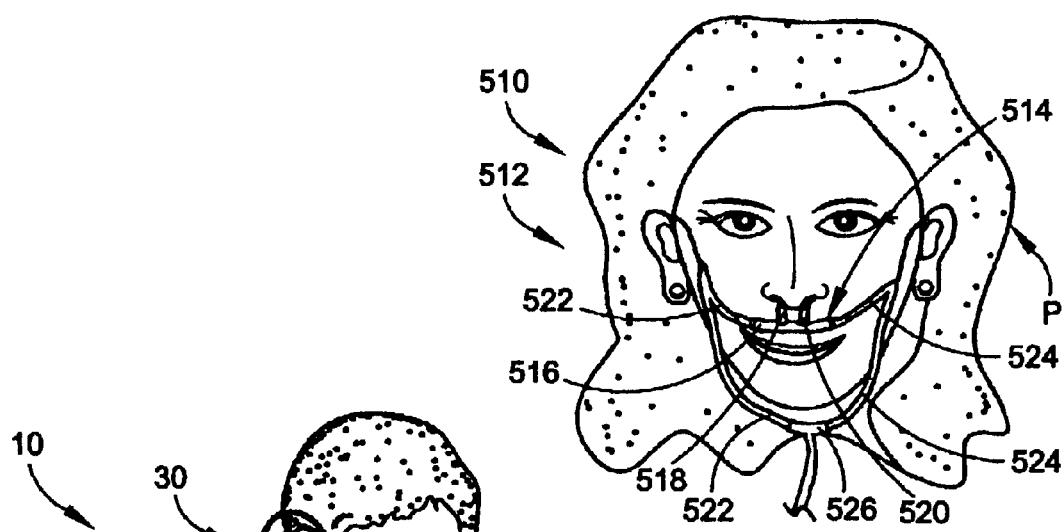
FIG. 1 depicts a frontal view of a patient's head showing a prior art typical prior art nasal cannula arrangement for delivering oxygen to a patient.

Before discussing the preferred embodiment of the present invention, it may be beneficial to briefly review a typical prior art oxygen delivery system 510 that utilizes a nasal cannula 512. In this regard, as best seen in FIG. 1, the nasal cannula 512 generally comprises a nosepiece or nasal assembly 514 having a hollow body member 516 with two upstanding nose prongs or nasal extension tubes 518 and 520 that are adapted to be placed in the nasal cavities of the patient P. Oxygen (from a source not shown) is supplied to the hollow body member 516 at ones of its end openings allowing the body member 516 to functions as a gas distribution manifold. Generally, a pair of gas supply tubes 522 and 524 are attached to the nosepiece 514, that is supported or held in place by extending the gas supply tubes 522 and 524 from the nosepiece 514 to respective ones of the ears of the patent P so the tubes 522 and 524 pass behind respective ones the ears of the patient P. The extension tubes 522 and 524 are bent downward behind the ears and traverse along the jaw area and are then secured together by a cinch 526 or an adjustable loop that is tightened below the chin of the patient to hold the nosepiece in place. The tubes are then joined in by a reducer (not shown) so that a single gas line is available to be attached to the oxygen or air source. From the foregoing, it should be understood that the looping tubes that extend around the ears of the user and along the jaw area of the patient and down to the neck area are uncomfortable and can be dislodged if the cinch 526 is not properly adjusted to tighten the loops sufficiently around the ears of the patient P in a somewhat uncomfortable manner.

Therefore the is a need for a new and improved oxygen delivery system that includes a nasal cannula that is easily adjusted for the comfort of the patient and that is not prone to falling off the face of the patient.

Figure 2:
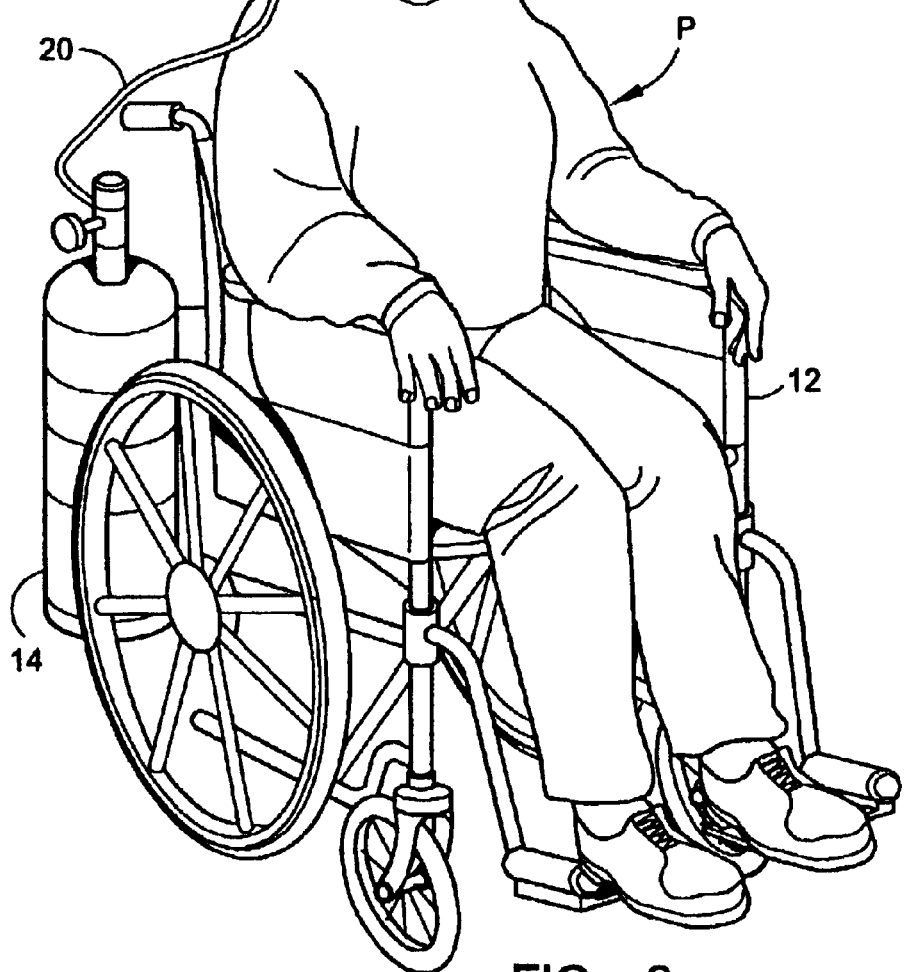
FIG. 2 depicts a perspective view of a patient using a preferred embodiment of the present invention.
Figure 3:
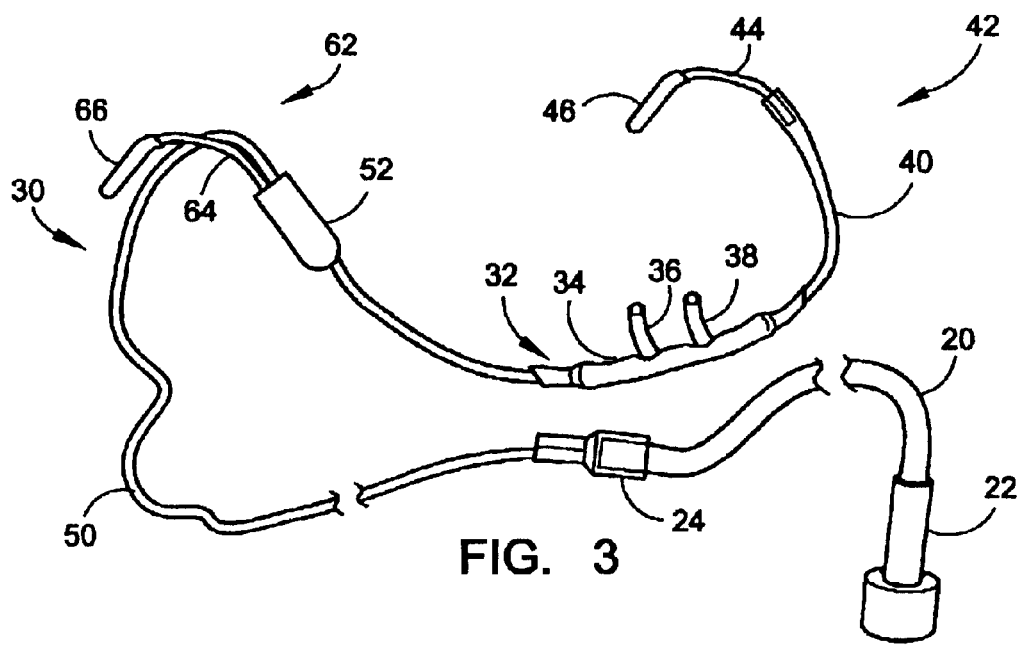
FIG. 3 depicts an oxygen delivery system, which is constructed in accordance with the present invention.
Figure 4:
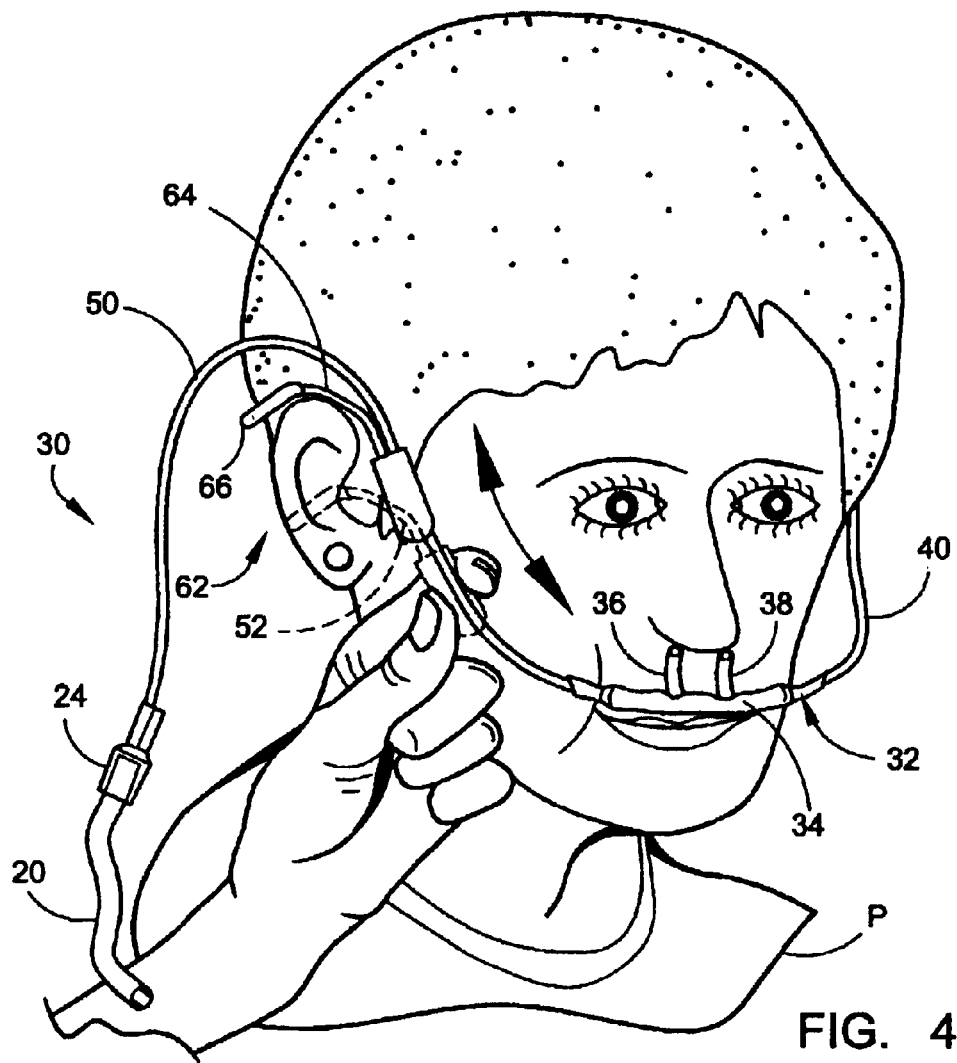
FIG. 4 depicts an adjustment step in the novel method of using the oxygen system.

Referring now to the drawings and more particularly to FIGS. 2–4, there is shown an oxygen delivery system 10 that is constructed in accordance with the present invention. The oxygen delivery system 10 is illustrated being utilized by a patient P who is sitting in a wheelchair 12 that is adapted to transport a source of oxygen or air shown generally at 14.

Considering now the oxygen delivery system 10 in greater detail, the oxygen delivery system 10, generally comprises a flexible tube member 20 that is connected at ones of its ends to a universal connector 22 that permits the flexible tube member 20 to be attached to the source of oxygen 14. A reduction connector 24 is connected to the other end of the flexible tube member 20 that permits the flexible tube member 20 to be attached to a nasal cannula assembly indicated generally at 30 that is adapted to be comfortably supported from the ears of the patient P as will be explained hereinafter in greater detail Considering now the nasal cannula assembly 30 in greater detail with reference to FIGS. 2–3, the nasal cannula assembly 30 generally includes a nasal delivery tube or nosepiece 32 that includes a hollow body member 34 with two upstanding nose prongs or nasal extension tubes 36 and 38. The nose prongs 34 and 36 are adapted to be placed in the nasal cavities of the patient P as best seen in FIG. 4. In this manner, when the nosepiece 32 is supported in the nasal cavities of the patient P it faciitates the delivery of oxygen to the lungs of the patient P in a comfortable and convenient manner. The nose prongs 34 and 36 are spaced apart from one another and have a sufficient length so as not to be dislodged from the nostrils of the patient. In this regard, the nose prongs 34 and 36 may be adjusted by cutting their ends with a pair of scissors (not shown) to a proper length to be comfortable to an individual patient, such as the patient P.

The hollow body member 34 is connected at its distal end in an airtight manner to an ear hook support tube 40 that is plugged at its distal end with an elongated flexible ear hook 42. The ear hook 42 includes a flexible extension member 44 and an ear cushion 46 that cooperate with one another so that the extension member 44 of the ear hook 42 may be looped over the ear of the patient P and supported therefrom in a comfortable manner with the ear cushion 46 resting against the back of the ear. In this manner the ear hook 42 can support the nosepiece 32 much in the same way as glass lens are supported but without the necessity of utilizing the bridge of the nose since the nosepiece is substantially lighter in weight that glasses.

The flexible extension member 44 is a solid flexible piece of plastic that has a diameter that is sufficiently large so that when the extension member 44 is inserted into the ear hook support tube 40 it can not be easily removed. To assure that the extension member 44 can not be removed from the ear book support tube 40, the tip of extension member 44 is coated with a sufficient amount of an adhesive to permanently fix the proximate end of the extension member 44 within the distal end of the ear hook support tube 40. It should be understood by those skilled in the art, that the ear hook 42 plugs the end of the ear support tube 40 in an airtight manner thereby assuring that airflow to the patient will be maintained without the need of a return tube. This arrangement eliminates the necessity of looping tubes around the ears of the user and along the jaw area and chin area thereby allowing the nosepiece 32 to be worn and support in a very comfortable manner.

The hollow body member 34 is coupled at its proximate end to a slider support tube 50 whose distal end is coupled in an airtight 24 manner to the reduction connector 24. In this manner, a fluid or air path is established between the oxygen source 14 and the nasal cannula assembly 30 when the slider support tube 50 is interconnected to the reduction connector 24. In the preferred embodiment of the present invention, the reduction connector 24 has been described as being attached to the flexible tube member 20. It should be understood however, by those skilled in the art, that the reduction connector 24 could be attached to the end of the slider support tube 50 as part of the nasal cannula assembly 30.

An ear hook slider 52 is slidably mounted to the slider support tube 50 and is adapted to carry along the slider support tube 50 another ear hook 62. The ear hook 62 is similar in construction to the ear hook 42 and includes a flexible extension member 64 and an ear cushion 66. In this case however, the adhesive end of the flexible member 64 is utilized to fix the proximate end of the extension member 64 within the ear hook slider 52. As will be explained herein after in greater detail, the ear hook slider 52 can pass along the slider support tube 50 to bring the ear hook 62 to an adjusted position that permits the ear hook 62 to he hooked comfortably over the other ear of the patient P so that the nosepiece 32 is support by both ear hooks 42 and 62 from the ears of the patient, much in the same manner as if the patient was wearing a pair of glasses. Again, however, since the nose piece 32 is much lighter in weight that a pair of glasses there is no need for any type of nose bridge support.

From the foregoing it should be understood, that the nasal cannula assembly 30 is light in weight, is easily attached to an oxygen source, such as the oxygen source 14, utilizing a single tube path, and can be easily adjusted to fit and be supported from the ears of any patient, such as the patient P. Another important feature of the preferred embodiment of the present invention is that the nasal cannula assembly 30 is compact, simple in construction and does not necessitate the utilization of looping tubes around the ears of the user and along the jaw area and chin area thereby allowing the nosepiece 32 to be worn and support in a very comfortable manner.

Considering now the novel method of using the oxygen delivery system 10 with reference to FIGS. 4–7, the patient P first inserts the nostril prongs 34 and 36 of the nosepiece 32 into his or her nostrils to make certain that their overall length is a comfortable fit within the nostrils. If not, the tips of the prongs 31 and 36 may be cut to adjust them to a sufficient length to facilitate the comfort of the patient. P. Next as best seen in FIG. 4, the patient P loops the ear hook 42 around his or her left ear so that the nasal cannula nosepiece 32 is supported by the left ear of the patient but without the nose prongs 34 and 36 lodged within the nostrils of the patient P.

The patient P then grasps the slider 52 between the thumb and forefinger of the patient as best seen in FIG. 5 and gently squeezes the slider 52 between the thumb and forefinger of the patient P, as best seen in FIG. 6. While squeezes the slider 52, the patient is then able to move the slider 52 up or down the slider support tube 50 as best seen in FIG. 7 to an adjusted position that permits the ear hook 62 to be looped comfortably around the other ear of the user. When the patient P has so adjusted the position of the ear hook 62, the patient P releases the slider 52 from between his or her thumb and forefinger and then loops the ear hook 62 around the right ear allowing the nose prongs 36 and 36 to be pulled up into the nostrils of the patient where they are disposed in a comfortable position and supported by the ears of the patient P.

In the final step, connecting the distal end of the slider support tube 50 to the reduction connector 24 connects the nasal cannula assembly 30 to the oxygen source 14. The patient P may then turn on the supply of air using an actuation knob allowing the free flow of oxygen to the nosepiece 32 for distribution into the lungs of the patient P.

Referring now to the drawings and more particularly to FIG. 8, there is illustrated another oxygen delivery system 110 that is substantially similar in construction to oxygen delivery system 10 except that a nosepiece 32, that includes a hollow body member 34 with prongs 36 and 38, is connected at its distal end in an airtight manner to an ear hook slider support tube 150. The ear hook slider support tube 150 is plugged at its distal end with a plug or stop 174 that will be described hereinafter in greater detail.

An ear hook slider 172 is slidably mounted to the slider support tube 150 and is adapted to carry along the slider support tube 150 another ear hook 142. The ear hook 142 is similar in construction to the ear hook 42 and includes a flexible extension member 144 and an ear cushion 146.

Considering now the method of using the oxygen delivery system 110 in greater detail with reference to FIG. 8, the patient P, the patient P first inserts the nostril prongs 34 and 36 of the nosepiece 32 into his or her nostrils to make certain that their overall length is a comfortable fit within the nostrils. If not, the tips of the prongs 34 and 36 may be cut to adjust them to a sufficient length to facilitate the comfort of the patient P. Next as best seen in FIG. 4, the patient P grasps the slider 172 between his or her thumb and forefinger and squeezes the slider 172. Next, the patient P adjust the position of the slider 172 up or down the slider support tube 150 until the ear hook 142 can be comfortably looped around the left ear of the patient. It should be noted at this point that the stop 174 includes a flange that prevents the slider 172 from being dislodged or slide off the distal end of the slider support tube 150. Once the patient P has adjusted the position of the ear hook 142 so that the nasal cannula nosepiece 32 is supported by the left ear of the patient, the patient P continues in substantially the same manner as previously described with reference to the oxygen delivery system 10. From the foregoing, it should be understood by those skilled in the art, that the oxygen delivery system 110 is substantially similar to oxygen delivery system 10 except that it includes two adjustable ear hook sliders, the slider 142 and another slider 172 that is substantially similar to slider 52.

Figure 9:
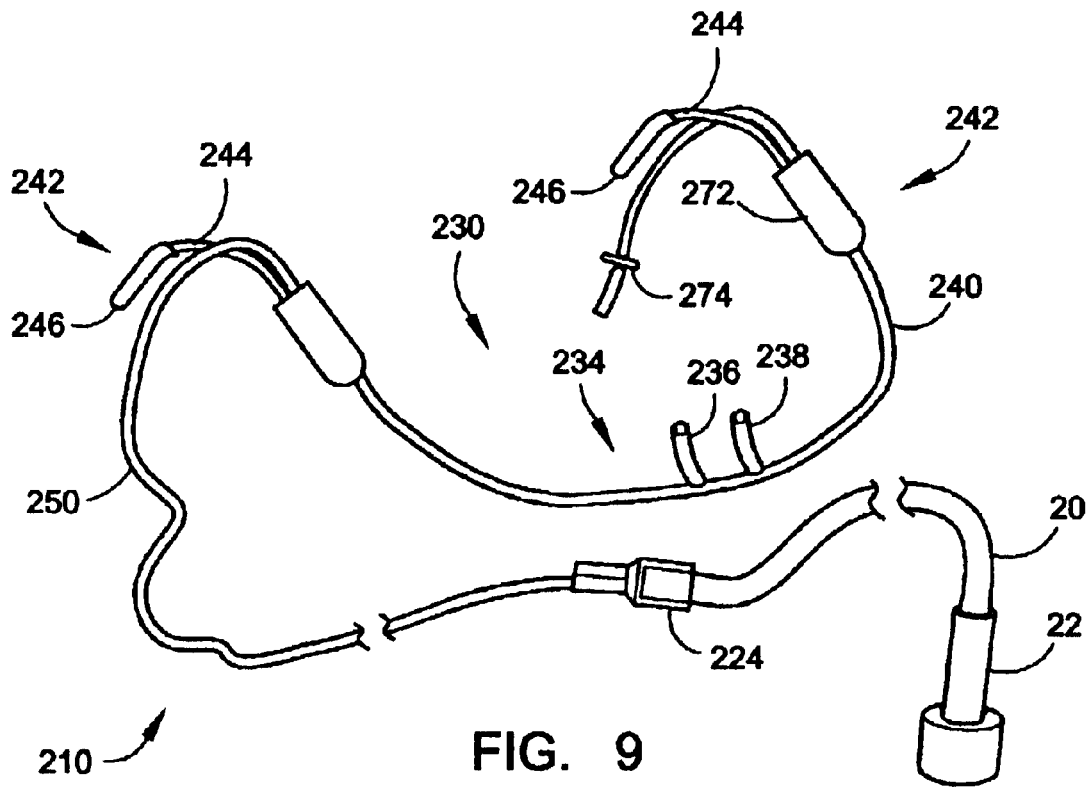
FIG. 9 depicts yet another oxygen delivery system, which is constructed in accordance with the present invention.

Referring now to the drawings and more particularly to FIG. 9 there is illustrated another oxygen delivery system 210 that is constructed in accordance with the present invention. The oxygen delivery system 210 is substantially similar to oxygen delivery system 10 except as hereinafter described.

The oxygen delivery system 10 generally comprises a nasal cannula assembly 230 that is adapted to be supported from the ears of a patient P in a secure comfortable manner. The nasal cannula assembly 230 includes a central manifold section 234 with a pair of upstanding nostril prongs 236 and 238. The nostril prongs are similar in construction to nose prongs 36 and 38 and will not be described hereinafter in greater detail.

The central manifold section 234 has a hollow body construction and is integrally connected between a pair of ear hook slider tube section 240 and 250 respectively. The distal end of the ear hook slider tube 740 terminates in a stop 274 while the distal end of the ear hook slider tube 250 terminates in an enlarger 224 that enables the nasal cannula assembly 230 to be connected to an oxygen source, such as the oxygen source 14. A pair of ear hook sliders 252 and 272 are slidably mounted to the slider tube sections 240 and 250 respectively. As the ear hook sliders 252 and 272 are substantially similar to ear hook sliders 52 and 172 respectively, they will not be described herein after in greater detail.

Figure 10:
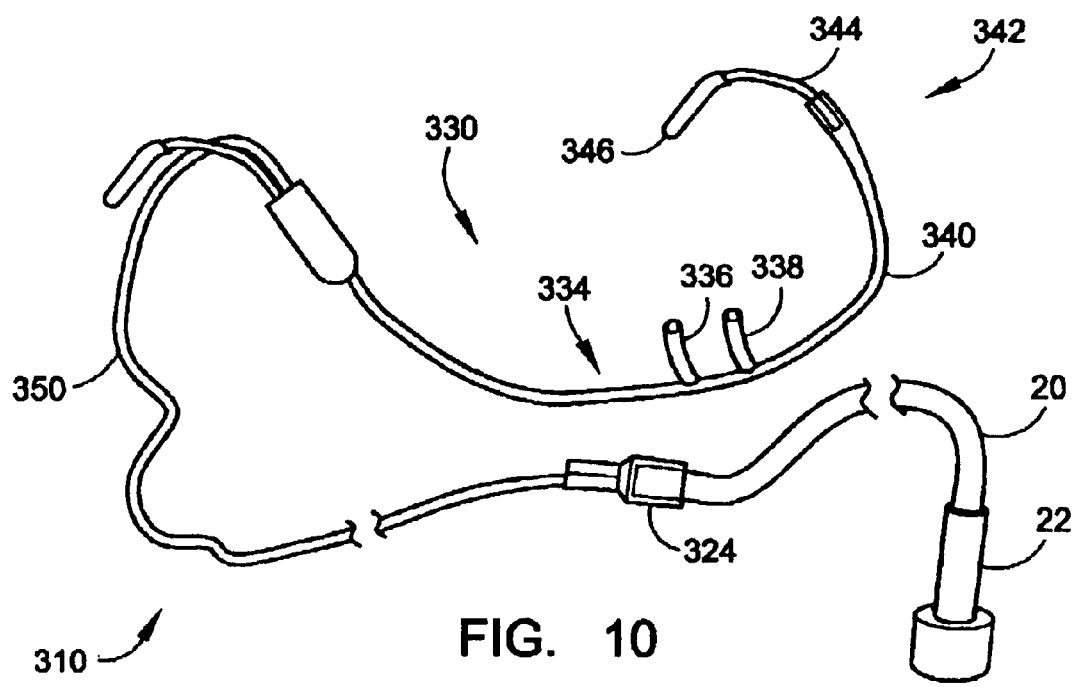
FIG. 10 depicts still yet another oxygen delivery system, which is constructed in accordance with the present invention.

Referring now to the drawings and more particularly to FIG. 10 there is illustrated another oxygen delivery system 310 that is constructed in accordance with the present invention. The oxygen delivery system 310 is substantially similar to oxygen delivery system 210 except as hereinafter described.

The oxygen delivery system 310 generally comprises a nasal cannula assembly 330 that is adapted to be supported from the ears of a patient P in a secure comfortable manner. The nasal cannula assembly 330 includes a central manifold section 334 with a pair of upstanding nostril prongs 336 and 338. The nostril prongs are similar in construction to nose prongs 36 and 38 and will not be described hereinafter in greater detail.

The central manifold section 334 has a hollow body construction and is integrally connected on its right side to an ear book slider tube section 340 and on its left side to an ear hook support tube section 350 respectively. The distal end of the ear hook support tube section 350 is plugged with an ear hook assembly 342. The ear hook assembly 342 includes an extension member 344 and an ear cushion member 346. As the ear hook assembly 342 is substantially similar to ear hook assembly 42 it will not be described hereinafter in greater detail.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A fluid delivery system, comprising:
   a nasal delivery tube for facilitating the delivery of fluids to the lungs of a user;
   an ear hook support tube coupled in an airtight manner to said nasal delivery tube and plugged at its distal end with an elongated flexible ear hook;
   a slider support tube coupled in an airtight manner to said nasal delivery tube and coupled at its distal end man airtight manner to a fluid supply system for delivering fluids to said nasal delivery tube through said slider support tube; and
   another elongated flexible ear hook slidably mounted to said slider support tube for sliding along said slider support tube to a user adjusted position; and
   wherein said another elongated flexible ear hook includes:
   a slider slidably mounted to said slider support tube for permitting a user to adjust the overall spacing between said elongated ear hook and said another elongated ear hook so they can loop over the ears of the user to facilitate supporting said nasal delivery tube substantially equally therebetween below the nostrils of the user.

2. A fluid delivery system according to claim 1, wherein said nasal delivery tube includes a pair of spaced apart nasal tips of sufficient length for insertion into the nostrils of a user.

3. A fluid delivery system according to claim 2, wherein said pair of spaced apart nasal tips have substantially smaller outer diameter than said nasal delivery tube.

4. A fluid delivery system according to claim 3, wherein said pair of spaced apart nasal tips are trimmable to custom fit the nostril depths of the user.

5. A fluid delivery system according to claim 1, wherein said ear hook support tube has a sufficient length to enable said elongated flexible ear hook to loop over the ear of the user to facilitate supporting one end of said nasal delivery tube in proximity to the face of the user.

6. A fluid delivery system according to claim 5, wherein said another flexible ear hook is mounted to said slider support tube by a pinchable slider.

7. A fluid delivery system according to claim 6, wherein said slider in an unpinched state holds said another flexible ear hook in a substantially stationary position relative to said flexible ear hook and said slider support tube.

8. A fluid delivery system according to claim 7, wherein said slider in a pinched state enables the user to slide said another elongated ear hook along said slider support tube to permit the user to adjust the overall spacing between said elongated ear hook and said another elongated ear hook so they can loop over the ears of the user to facilitate supporting said nasal delivery tube substantially below the nose of the user and in close proximity to the nostrils of the user.

9. A fluid delivery system according to claim 5, wherein said slider support tube has another sufficient length to enable said another elongated flexible ear hook to be positioned on said slider support tube so that said nasal delivery tube is suspended directly below the nostrils of a user when said elongated flexible ear hook and said another elongated flexible ear hook are looped over opposite ears of the user.

10. A fluid delivery system according to claim 9, where in said sufficient length of said ear hook support tube is substantially less than said sufficient length of said slider support tube.

* * * * *